United States Patent [19]

Sunshine et al.

[11] Patent Number: 4,871,733

[45] Date of Patent: Oct. 3, 1989

[54] COUGH/COLD MIXTURES COMPRISING NON-SEDATING ANTIHISTAMINE DRUGS

[75] Inventors: Abraham Sunshine, New York; Eugene M. Laska, Larchmont; Carole E. Siegel, Mamaroneck, all of N.Y.

[73] Assignee: Analgesic Associates, Larchmont, N.Y.

[21] Appl. No.: 230,887

[22] Filed: Aug. 11, 1988

Related U.S. Application Data

[60] Division of Ser. No. 42,120, Apr. 24, 1987, Pat. No. 4,783,465, which is a continuation-in-part of Ser. No. 887,205, Jul. 24, 1986, Pat. No. 4,738,966, which is a division of Ser. No. 752,546, Jul. 8, 1985, Pat. No. 4,619,934, which is a division of Ser. No. 598,502, Apr. 9, 1984, Pat. No. 4,552,899.

[51] Int. Cl.$^4$ .................... A61K 31/19; A61K 31/44; A61K 31/55; A61K 31/445; A61K 31/495; A61K 31/505

[52] U.S. Cl. .................... 514/212; 514/255; 514/256; 514/290; 514/315; 514/336; 514/570

[58] Field of Search ............... 514/255, 256, 290, 315, 514/336, 520, 212

*Primary Examiner*—Stanley J. Friedman
*Attorney, Agent, or Firm*—Burns, Doane, Swecker & Mathis

[57] ABSTRACT

Pharmaceutical compositions and methods of using same comprising a non-steroidal anti-inflammatory drug in combination with a non-sedating antihistamine and optionally one or more other active components selected from a decongestant, cough suppressant (antitussive) or expectorant are provided for the relief of cough, cold, cold-like and/or flu symptoms and the discomfort, pain, headache, fever and general malaise associated therewith.

29 Claims, No Drawings

COUGH/COLD MIXTURES COMPRISING NON-SEDATING ANTIHISTAMINE DRUGS

This application is a division of U.S. Ser. No. 042,120, filed Apr. 24, 1987, now U.S. Pat. No. 4,783,465; which is a continuation-in-part of U.S. Ser. No. 887,205, filed July 24, 1986, now U.S. Pat. No. 4,738,966; which is a division of U.S. Ser. No. 752,546, filed July 8, 1985, now U.S. Pat. No. 4,619,934; which is a division of U.S. Ser. No. 598,502, filed Apr. 9, 1984, now U.S. Pat. No. 4,552,899.

BACKGROUND OF THE INVENTION

The present invention relates generally to novel pharmaceutical compositions of matter comprising one or more non-steroidal anti-inflammatory drugs (NSAID) in combination with a non-sedating antihistamine and optionally one or more other active components selected from a sympathomimetic drug (nasal decongestant, bronchodilator) cough suppressant and/or expectorant, optionally in combination with suitable pharmaceutically acceptable non-toxic carriers or excipient, and to methods of using said compositions in the treatment, management or mitigation of cough, cold, cold-like and/or flu symptoms and the discomfort, pain, headache, fever and general malaise associated therewith.

Applicants' earlier application, now U.S. Pat. No. 4,619,934 was directed to one or more NSAID's in combination with a conventional antihistamine and other optional components. Applicants have now discovered that the non-sedating antihistamines, which are pharmacologically and chemically distinct from the conventional antihistamines, in combination with one or more NSAID's offers significant advantages in the treatment, management or mitigation of cough, cold, cold-like and/or flu symptoms and the discomfort, pain, fever and general malaise associated therewith. It is well known that the conventional antihistamines may cause drowsiness or marked drowsiness. While this may be an advantage at bedtime, if taken during the day, the label recommends that a patient use caution when driving a motor vehicle or operating machinery. The combination of a non-sedating antihistamine and an NSAID is therefore particularly advantageous for daytime administration.

Non-narcotic analgesics, most of which are also known as non-steroidal anti-inflammatory drugs, are widely administered orally in the treatment of mild to severe pain. Within this class, the compounds vary widely in their chemical structure and in their biological profiles as analgesics, anti-inflammatory agents and antipyretic agents. Among the most commonly used members of the non-narcotic analgesic class of drugs are aspirin and acetaminophen. Aspirin, acetaminophen and salicylamide are among the drugs that have heretofore been included as the pain reliever and fever-reducing component in conventional cough/cold multisymptom alleviating compositions.

However, a number of alternative non-narcotic agents offering a variety of advantages over these conventionally employed non-narcotic analgesic antipyretics have now been developed. The principal advantages of these non-steroidal anti-inflammatory drugs include not only the clinically superior analgesic, anti-inflammatory and antipyretic activity of these agents compared to aspirin and acetaminophen, but also a minimization of the adverse side effects experienced with these conventional agents; more specifically, the gastrointestinal ulcerations experienced with aspirin and the hepatic toxicity prevalent with the chronic use of acetaminophen.

Exemplary prior art cough/cold formulations containing aspirin or acetaminophen include Coricidin ®, Coricidin D ®, Comtrex ®, Dristan ®, Daycare ®, Cotylenol ®, Sinubid ® and the like. These formulations generally contain in addition to aspirin, acetaminophen or salicylamide, one or more conventional antihistaminics, decongestants, cough suppressants, antitussives and expectorants.

While aspirin and acetaminophen have been utilized in these previous compositions, it has not been heretofore proposed to use any of the newer non-steroidal anti-inflammatory drugs (i.e., excluding aspirin, acetaminophen and phenacetin) in the preparation of advantageous cough/cold pharmaceutical compositions.

SUMMARY OF THE INVENTION

It is, therefore, a primary object of the present invention to provide pharmaceutical compositions of matter comprising an analgesically effective amount of a non-steroidal anti-inflammatory drug in combination with a non-sedating antihistamine, and optionally one or more active components selected from a decongestant, cough suppressant, expectorant and, further optionally including pharmaceutically acceptable carriers therefor.

It is a further object of the present invention to provide methods for the symptomatic relief of cough, cold, cold-like and flu symptoms and the discomfort, pain, headache, fever and general malaise associated therewith, by the administration of preselected dosages of the pharmaceutical compositions of the present invention. Cold-like symptoms as used herein refers to coryza, nasal congestion, upper respiratory infections, allergic rhinitis, otitis, sinusitis, etc.

Another object of the present invention is to provide suitable dosage unit forms of one or more NSAID's in combination with a non-sedating antihistamine and optionally one or more active components selected from a decongestant, cough suppressant or expectorant adapted for convenient oral administration.

DETAILED DESCRIPTION OF THE INVENTION

More specifically, the applicants herein have found that certain non-steroidal anti-inflammatory agents are ideally suited for use in cough/cold formulations by reason of their enhanced analgesic anti-inflammatory and antipyretic activity and low incidence of untoward side effects, particularly at the optimum dosages provided for in the present invention, compared to aspirin or acetaminophen.

For example, the antipyretic effectiveness of ibuprofen in comparison to aspirin and to acetaminophen has been studied. Gaitonde, B. B. et al, "Antipyretic Activity of Ibuprofen (Brufen)", *J. ASS. Physicians, India* (1973) 21: 579-584 describes the results of two randomized, double-blind, parallel studies comparing the antipyretic efficacy of ibuprofen to that of aspirin. In the first study, 17 adult patients with fever of 100° F. or more (orally) due to upper respiratory tract infections were given a capsule containing either ibuprofen 200 mg (7 patients) or aspirin 300 mg (10 patients). In the second study, 11 adult patients with resistant, chronic gonococcal urethritis were inoculated with T.A.B. vaccine (containing *S. typhosa* and paratyphi A+B microorganisms). Once peak temperature was reached as indicated by cessation of rigors, each patient received either ibuprofen 400 mg (5 patients) or aspirin 600 mg (6 patients).

In the patients with upper respiratory tract infections antipyretic effect from both treatments began approximately one hour after dosing. The temperature curves following both treatments were very similar, with the maximum decrease in temperature being reached 3½ hours following aspirin 300 mg and 4½ hours following ibuprofen 200 mg. In the second study, where the fever was induced by the vaccine, the temperature response curves were again very similar with the mean maximum fall in temperature occurring at about three hours with both treatments. The temperature did not rise, however, at five and six hours in the ibuprofen 400 mg treated patients. In the group treated with aspirin 600 mg there was a rise in temperature at five hours and a further rise at six hours although at the six hours observation time there were measurements on only three of the six aspirin patients.

Sheth, U. K. et al, "Measurement of Antipyretic Activity of Ibuprofen and Paracetamol in Children", *J. Clin. Pharmacol.*, 20: 672–675 (1980) reported on a randomized, open label study in which the antipyretic activity of ibuprofen was compared to that of acetaminophen in 22 children aged two to eight years suffering from fever due to upper respiratory tract infection and other causes. Both ibuprofen and acetaminophen at the doses used produced a significant fall in the initial temperature, continuing to 12 hours. The rate of fall and maximum effect of the two drugs were similar. Ibuprofen, however, was more effective than acetaminophen at these doses at six and eight hours after drug administration, indicating a longer duration of effect on ibuprofen.

The superiority the analgesic properties of various of the non-narcotic analgesics belonging to the non-steroidal anti-inflammatory drug class in comparative studies with placebo, aspirin and acetaminophen in patients with various types of pain including headache, aches and pains associated with colds, dental pain, postpartum pain, musculoskeletal pain, menstrual cramping, and so forth, is well documented in the literature.

A report by Busson, M., "A Double Blind Multicentre Comparison of Ibuprofen and Placebo in Colds and Non-specific Headaches", The Boots Company, Ltd. Research Report (1982) presents the results of a double-blind randomized crossover study of the analgesic efficacy of ibuprofen 200 mg or ibuprofen 400 mg compared to placebo in 332 patients with self-diagnosed headaches (161 patients) and colds (171 patients). In addition to a composite analysis of the entire population, subgroup analyses were performed on these patients whose primary compliant was headache and on those patients complaining of colds. The data show that ibuprofen at both doses produced statistically significant improvement both in headache and in aches and pains associated with colds compared with placebo, in all composite and subgroup comparisons except the 200 mg ibuprofen vs. placebo in cold patients in the parallel groups (first treatment only) comparison. Patient preference in the composite, headache, and cold groups was also significantly in favor of both ibuprofen treatments as compared to placebo.

Cooper in 1977 found that for pain relief ibuprofen 400 mg had a greater peak effect and longer duration of action than aspirin 650 mg. Cooper, S. A., Needle, A. E., Kruger, G. O. 1977. "An Analgesic Relative Potency Assay Comparing Aspirin, Ibuprofen and Placebo." *J. Oral Surg.* 35: 898–903. Cooper in another study in 1982 found 400 mg of ibuprofen to be more effective than aspirin 650 mg. Cooper, S. A., Engel, J., Ladov, M., Precheur, H., Rosenheck, A., Rauch, D. 1982. "Analgesic Efficacy of an Ibuprofen-codeine Combination." [*Pharmacotherapy* 2: 162–67. Sunshine et al found ibuprofen to be significantly superior to aspirin in the relief of postepisiotomy pain. Sunshine, A. et al, *Clinical Pharmacology and Therapeutics*, 24:254–250, 1983.

Dionne in 1982 found ibuprofen to be more effective than acetaminophen in delaying the onset and intensity of post-operative dental pain. Dionne, R. A., Campbell, R. A., Cooper, S. A., Hall, D. L., Buckingham, B. "Suppression of Post operative Pain by Preoperative Administration of Ibuprofen in Comparison to Placebo, Acetaminophen and Acetaminophen Plus Codeine." *J. Clin. Pharmacol.* (In press).

Naproxen sodium 550 mg was compared with 650 mg of aspirin and was found to provide earlier and better pain relief than aspirin by Sevelius, H., *J. Clin. Pharmacol.* 20: 480–485, 1980. "Comparative Analgesic Effects of Naproxen Sodium, Aspirin and Placebo."

Flurbiprofen 50 and 100 mg was significantly more effective than aspirin 600 mg. Flurbiprofen 25 mg was slightly less effective than aspirin 600 mg. Sunshine, A., Olson N. Z., Laska, E. M., Zighelboim, I., DeCastro, A., Desarrazin, C., *Pharmaco Ther.* 3: 177–181. "Analgesic Effect of Graded Doses of Flurbiprofen in Postepisiotomy Pain."

More recently, ibuprofen 200 mg has become available over-the-counter (OTC) and at 200 to 400 mg is indicated for the temporary relief of minor aches and pains associated with the common cold, headache, toothache, muscular aches, backache, for the minor pain of arthritis, for the pain of menstrual cramps and for reduction of fever. While these reported findings with respect to the outstanding analgesic properties of the non-steroidal anti-inflammatory drugs compared to aspirin or acetaminophen have prompted the widespread acceptance and usage of these newer non-narcotic analgesics, as single entities, for the treatment and management of acute and chronic pain as well as inflammatory states, notably rheumatoid arthritis and osteoarthritis, the utilization of these agents in cough/cold compositions for multi-symptom relief has not heretofore been considered, this despite the fact that ibuprofen's and other NSAID's antipyretic and analgesic properties have been well known for more than a decade.

The non-steroidal anti-inflammatory drugs for use in the pharmaceutical compositions and methods of use of the present invention may be selected from any of the following categories:

(1) The propionic acid derivatives;
(2) The acetic acid derivatives;
(3) The fenamic acid derivatives;
(4) The biphenylcarboxylic acid derivatives; and
(5) The oxicams.

Accordingly, the term "NSAID" as used herein is intended to mean any non-narcotic analgesic non-steroidal anti-inflammatory compound, including the pharmaceutically acceptable non-toxic salts thereof, falling within one of the five structural categories above but excluding aspirin, acetaminophen and phenacetin.

The specific compounds falling within the foregoing definition of the non-steroidal anti-inflammatory drugs for use in the present invention are well known to those skilled in the art and reference may be had to various literature reference sources for their chemical structures, pharmacological activities, side effects, normal dosage ranges, etc. See, for example, *Physician's Desk Reference*, 35th Edition, (1981); *The Merck Index*, 9th Edition, Merck and Company, Rahway, N.J. (1976); and *Cutting's Handbook of Pharmacology*, 6th Edition, Ed. T. Z. Czacky, M.D., Appleton-Century-Crofts, New York (1979), Chapter 49: 538–550.

Of the propionic acid derivatives for use herein, ibuprofen, naproxen, flurbiprofen, fenoprofen, ketoprofen, fenbufen, and fluprofen may be mentioned as particularly preferred compounds.

Of the acetic acid derivatives, presently preferred members include tolmetin sodium, sulindac and indomethacin.

Of the fenamic acid derivatives, particularly preferred compounds include mefenamic acid and meclofenamate sodium.

The particularly preferred biphenylcarboxylic acid derivatives for use in the present invention include diflunisal and flufenisal.

The particularly advantageous oxicams include piroxicam, sudoxicam and isoxicam.

Of course, it will be appreciated by those skilled in the art, that any of the foregoing compounds may be utilized in the form of their pharmaceutically acceptable salt forms, e.g., $-COO^-Na^+$, $-COO^-K^+$, and the like.

Of the foregoing non-steroidal anti-inflammatory drugs, in the practice of the preferred embodiments of the present invention, ibuprofen and naproxen are most preferred.

With respect to the dosage amount of the non-steroidal anti-inflammatory drugs in the compositions of the invention, although the specific dose will vary depending upon the age and weight of the patient, the severity of the symptoms, the incidence of side effects and the like, for humans, typical effective analgesic amounts of presently preferred NSAID's for use in unit dose compositions of the invention are about 100–500 mg diflunisal, about 50–600 mg ibuprofen, most preferably 100–400 mg, about 125–500 mg naproxen, about 25–100 mg flurbiprofen, about 50–100 mg fenoprofen, about 10–20 mg piroxicam, about 125–250 mg mefenamic acid, about 100–400 mg fenbufen or about 25–50 mg ketoprofen; however, greater or lesser amounts may be employed if desired or necessary. With respect to the compounds set forth hereinabove falling within the propionic acid derivative category, suitable dosage ranges for these compounds will generally fall within the range of 25 mg to 600 mg in each unit dose.

A complete description of the various NSAID's, including acceptable analgesically effective amount thereof for use in unit dose compositions of the present invention also appears in applicants' U.S. Pat. Nos. 4,486,436 and 4,522,826, and the entire disclosures of which are incorporated herein by reference.

The non-sedating antihistamines are pharmacologically and chemically distinct from the conventional antihistamines. The non-sedating antihistamines represent a new generation of drugs which specifically block $H_1$-histamine receptors and do not cause sedation. The sedative properties of conventional antihistamines are well known and for daytime use especially represent a significant disadvantage during treatment. The FDA's Tentative Final Monograph has proposed that the labeling for category I OTC antihistamines, in general, carry the warning, "May cause drowsiness; alcohol may increase the drowsiness effect. Avoid alcoholic beverages while taking this product. Use caution while driving a motor vehicle or operating machinery." The non-sedating antihistamines are only peripherally active, that is, they do not penetrate the blood-brain barrier in significant amounts to cause drowsiness. Thus, unlike the conventional antihistamines, the labeling for the non-sedating antihistamines do not carry warnings to patients to refrain from driving a car or operating machinery during therapy or concomitantly using alcohol or other central nervous system depressants as they do for conventional antihistamines. Nor are the non-sedating antihistamines contraindicated in patients who are suffering from glaucoma, bronchial asthma, or prostatic hypertrophy.

In vivo studies have shown that the non-seadating antihistamines preferentially bind to peripheral rather than central $H_1$-histamine receptors. Since conventional antihistamines which produce sedation have greater affinities for central $H_1$-histamine receptors, the lesser penetration of the non-sedating antihistamines into the central nervous system may be responsible for their apparent lack of central nervous system effects. In addition, as a general rule, the non-sedating antihistamines possess minimal or no antiserotoninergic, anticholinergic or antiadrenergic activity. Psychomotor and visual function tests in man have shown that the non-sedating antihistamines do not impair psychomotor performance or adversely affect subjective feelings, in contrast to conventional antihistamines which were active in these tests. The non-sedating antihistamines neither affect the EEG as sedative antihistamines are known to do, nor interact with other depressant drugs (such as alcohol or benzodiazepines) to produce enhanced depressant effects.

The lack of sedative effects from the non-sedating antihistamines may be especially useful in children, where prescribing of conventional antihistamines is often hindered because of the daytime sedation they produce.

The non-sedating antihistamines include acrivastine, AHR-11325, astemizole, azatadine, azelastine, cetirizine, ebastine, ketotifen, lodoxamide, loratidine, levocabastine, mequitazine, oxatomide, setastine, tazifylline, temelastine, and terfenadine. Representative chemical structures for many of the non-sedating antihistamines are presented in Table I.

TABLE I

Non-Sedating Antihistamines

| Common Name or Generic Name | Chemical Structure | Chemical Name |
|---|---|---|
| acrivastine | 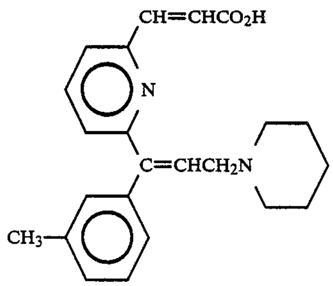 | 3-(6-(1-(4-methylphenyl)-3-(1-pyrrolidinyl)-1-propenyl)-2-pyridinyl)-2-propenoic acid |
| astemizole | 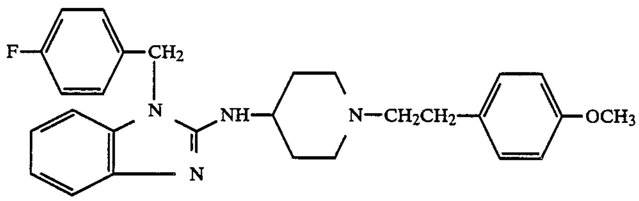 | 4-(2-(4-((1-((4-fluorophenyl)methyl)-1H—benzimidazol-2-yl)amino)-1-piperidinyl)ethyl)-phenol |
| azatadine | 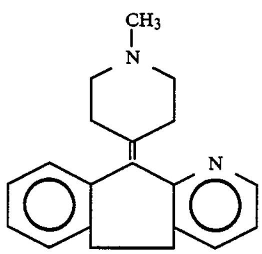 | 6,11-dihydro-11-(methyl-4-piperidinylidene)-5H—Benzo(5,6)cyclohepta(1,2-b)-pyridine [(Z)—2-butenedioate (1:2)] 6,11-dihydro-11-(1-methyl-4-piperidylidene)-5H—Benzo(5,6)cyclohepta(1,2-b)-pyridine [maleate (1:2)] |
| ketotifen | 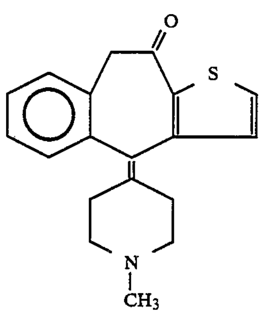 | 4,9-dihydro-4-(1-methyl-4-piperidinylidene)-10H—benzo(4,5)cyclohepta(1,2-b)-thiophen-10-one [(E)—2-butenedioate (1:1)] |
| lodoxamide | 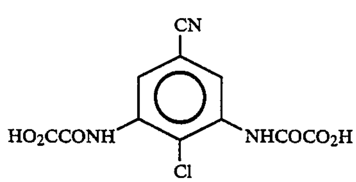 | 2,2'-((2-chloro-5-cyano-1,3-phenylene)diimino)bis(2-oxo-acetic acid) compound with 2-amino-2-(hydroxymethyl)-1,3-propanediol (1:2) |
| levocabastine | 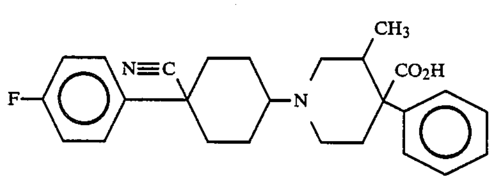 | 1-(4-cyano-4-(4-fluorophenyl)cyclohexyl)-3-methyl-4-phenyl-4-piperidinecarboxylic acid |

TABLE I-continued
Non-Sedating Antihistamines

| Common Name or Generic Name | Chemical Structure | Chemical Name |
|---|---|---|
| mequitazine | 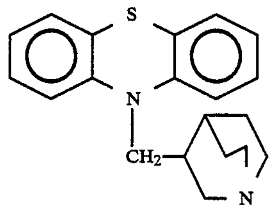 | 10-(1-azabicyclo(2.2.2)oct-3-yl-methyl)-10H—phenothiazine |
| oxatomide | 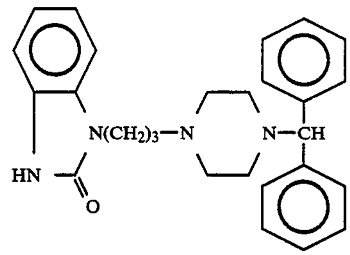 | 1-(3-(4-(diphenylmethyl)-1-piperazinyl)propyl)-1,3-dihydro-2H—benzimidazol-2-one |
| tazifylline | 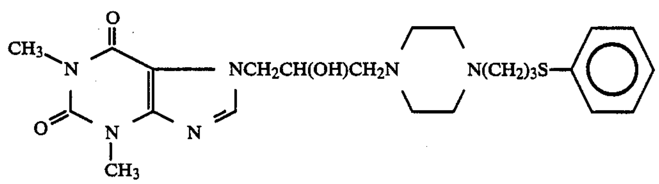 | 3,7-dihydro-7-(2-hydroxy-3-(4-(3-(phenylthio)propyl)-1-piperazinyl)propyl)-1,3-dimethyl-1H—purine-2,6-dione |
| temelastine | 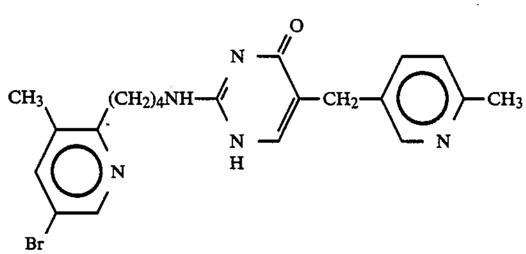 | 2-((4-(5-bromo-3-methyl-2-pyridinyl)butyl)amino)-5-((6-methyl-3-pyridinyl)methyl)-4(1H)—pyrimidinone |
| terfenadine | 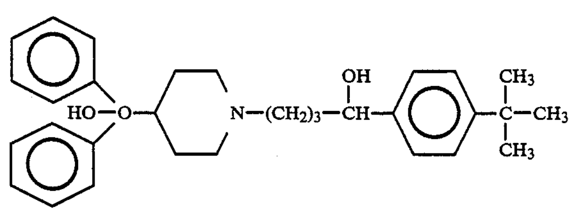 | alpha-(4-(1,1-dimethylethyl)phenyl)-4-(hydroxydiphenylmethyl)-1-piperidinebutanol |
| | | (8-chloro(6,11-dihydro-11-(1-carboethoxy-4-piperidylidene)-5-H—benzo(5,6[cyclohepta(1,2-b]-pyridine) |

The preferred non-sedating antihistamines for use in the practice of the present invention are astemizole and terfenadine. Terfenadine is marketed in the United States as Seldane, a registered trademark of Merrill Dow Pharmaceuticals.

The amount of the non-sedating antihistamine useful in the practice of the present invention generally ranges from about 1 mg to about 1000 mg depending on the specific non-sedating antihistamine selected; however, greater or lesser amounts may be employed if desired or necessary.

The recommended dosage of terfenadine, for instance, is 60 mg orally (1 tablet or 10 ml of suspension) once or twice daily. In children aged 6 to 12 years, the dosage is 30 mg (5 ml of suspension) to 60 mg twice daily depending on body weight. In children aged 3 to 5 years, the dosage is 15 mg twice daily. Some studies suggest doses ranging from 20 mg thrice daily to 200 mg thrice daily. Terfenadine has also been demonstrated to be of value in exercise-induced asthma when given orally in a single dose of 120 mg or 180 mg.

The usual dose of astemizole is 10 mg to 25 mg once daily. Astemizole has a half-life of several days and thus it may be given as a single tablet daily, which is an important advantage in obtaining greater patient compliance; therefore, it can advantageously be added to one of the longer acting NSAID's. The recommended dose of mequitazine is 5 mg twice daily. SK&F 93944 is being evaluated in humans at a dose of 100 mg once or twice daily.

The cough/cold pharmaceutical compositions of the present invention comprise, in addition to the non-steroidal anti-inflammatory drugs, at least one non-sedating antihistamine as an active ingredient and optionally one or more active ingredients from the following pharmacological classes: sympathomimetics (decongestants), cough suppressants-antitussives and expectorants. Typical therapeutically active components from these categories, along with their usual adult dosage, for use in the pharmaceutical compositions and methods of the invention are set forth in the following Table II. Of course, sustained release formulations would contain higher doses than those set forth in Table II.

These non-sedating antihistamines could enhance the analgesic properties of the NSAID's, such as ibuprofen and naproxen, as has been observed for conventional antihistamines. Notably, diphenhydramine, a conventional antihistamine, in combination with a non-steroidal anti-inflammatory drug, ibuprofen, has already been demonstrated by Applicants to produce a synergistically enhanced analgesic response in a mammalian organism. Again compare their U.S. Pat. No. 4,522,826.

TABLE II

| DRUG (FORM-SALT) | ACTION | PREPARATIONS | USUAL SINGLE DOSE ADULT |
|---|---|---|---|
| pseudoephedrine (sulfate, HCl) | D | Tablet, Capsule 30 mg, 60 mg, 120 mg (sustained action) | 30–120 mg |
| phenylpropanolamine | D | Tablet, Capsule, Elixir, 25 mg, 50 mg, 12.5 mg/5 cc | 5–50 mg |
| phenylephrine (bitartrate, tannate, HBr, HCl) | D | Tablet, Capsule Elixir, 5 mg, 10 mg, 25 mg, 5 mg/5 cc | 5–25 mg |
| caramiphen (edisylate) | CS | Capsule, Elixir 20 mg, 5 mg/5 cc | 5–20 mg |
| dextromethorphan (HBr) | CS | Tablet, Capsule, Elixir 15 mg, 30 mg 15 mg/5 cc | 2.5–30 mg |
| codeine (phosphate, sulfate) | CS | Tablet, Elixir 10 mg 10 mg/5 cc | 10–20 mg |
| benzonatate | CS | Capsule 100 mg | 100 mg |
| chlophedianol (HCl) | CS | Elixir 25 mg/5 cc | 25 mg |
| terpin hydrate | E | Tablet, Elixir 300 mg | 85–300 mg |
| quaifenesin (glyceryl quaiacolate | E | Tablet, Capsule, Elixir, 100 mg, 100 mg/5 cc | 25–200 mg |
| potassium (Iodide) (citrate) | E | Tablet, Elixir 100 mg, 100 mg/5 cc | 150–300 mg |
| potassium guaicolsulfonate | E | Elixir 80 mg/5 cc | 45–300 mg |

D = decongestant
CS = cough suppressant
E = expectorant

In the pharmaceutical compositions and methods of the present invention, the foregoing active ingredients will typically be administered in admixture with suitable pharmaceutical diluents, excipients or carriers (collectively referred to herein as "carrier" materials) suitably selected with respect to the intended form of administration, i.e., oral tablets, capsules, elixirs, syrups, suspensions, etc. and consistent with conventional pharmaceutical practices. For instance, for oral administration in the form of tablets or capsules, the active drug components may be combined with any oral nontoxic pharmaceutically acceptable inert carrier such as lactose, starch, sucrose, cellulose, magnesium stearate, dicalcium phosphate, calcium sulfate, mannitol, ethyl alcohol (liquid forms) and the like. Moreover, when desired or necessary, suitable binders, lubricants, disintegrating agents and coloring agents can also be incorporated in the mixture. Suitable binders include starch, gelatin, natural sugars, corn sweeteners, natural and synthetic gums such as acacia, sodium alginate, carboxymethylcellulose, polyethylene glycol and waxes. Among the lubricants there may be mentioned for use in these dosage forms, boric acid, sodium benzoate, sodium acetate, sodium chloride, etc. Disintegrators include, without limitation, starch, methylcellulose, agar, bentonite, guar gum, etc. Sweetening and flavoring agents and preservatives can also be included where appropriate.

Of course, additionally, the compositions of the present invention may be formulated in sustained release form to provide the rate controlled release of any one or more of the components to optimize the therapeutic effects, i.e., analgesia, antihistaminic, etc. while minimizing undesirable side effects. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

As representative suitable formulations consistent with the objects, features and advantages of the present invention, the following non-limiting examples are provided.

EXAMPLE 1

Ibuprofen—200 mg
Dextromethorphan hydrobromide—30 mg

Guaifenesin—100 mg
Terfenadine—60 mg
Triturate active ingredients and q.s. with lactose to selected capsule size.

EXAMPLE 2

In each fluid ounce:
Naproxen (sodium)—250 mg
Dextromethorphan hydrobromide—30 mg
Astemizole—10 mg
Orange flavoring and alcohol 10% v/v.

EXAMPLE 3

Ibuprofen—200 mg
Terfenadine—60 mg
Triturate active ingredients and q.s. with lactose to selected capsule size.

From the foregoing, other typical acceptable pharmaceutical formulations will be apparent to those skilled in the art of pharmaceutical formulations.

While this invention has been described and illustrated with reference to certain preferred embodiments thereof, those skilled in the art will appreciate that various changes, modifications and substitutions can be made therein without departing from the spirit of the invention. For example, effective dosages other than the preferred ranges set forth hereinabove with respect to the active ingredients may be applicable as a consequence of variations of the responsiveness of the mammal treated, severity of symptoms, dosage related adverse effects, if any, observed and similar considerations. Accordingly, such expected variations or differences in the practice of the present invention and the results obtained are contemplated in accordance with the objects and practices of the present invention. It is intended, therefore, that the invention be limited only by the scope of the claims which follow.

What is claimed is:

1. A pharmaceutical composition of matter for use in the treatment of cough, cold, cold-like and/or flu symptoms and the discomfort, pain, fever and general malaise associated therewith, in a mammalian organism, and adapted for unit dosage oral administration, said composition comprising (i) and analgesically and anti-inflammatory effective amount of at least one of the propionic acid NSAIDs, ibuprofen, naproxen, benoxaprofen, flurbiprofen, fenoprofen, fenbufen, ketoprofen, indoprofen, pirprofen, carprofen, oxaprozin, pranoprofen, miroprofen, tioxaprofen, alminoprofen, tiaprofenic acid, fluprofen and bucloxic acid or pharmaceutically acceptable salt thereof, in combinatory immixture with (ii) an antihistaminically effective amount of at least one of the non-sedating antihistamines, AHR-11325, azelastine, ebastine, lodoxamide, levocabastine, mequitazine, oxatomide, setastine, tazifylline, or pharmaceutically acceptable salt thereof.

2. The pharmaceutical composition defined by claim 1, said non-steroidal anti-inflammatory drug comprising ibuprofen or pharmaceutically acceptable salt thereof.

3. The pharmaceutical composition defined by claim 1, said non-steroidal anti-inflammatory drug comprising naproxen or pharmaceutically acceptable salt thereof.

4. The pharmaceutical composition defined by claim 1, comprising at least 25 mg of said non-steroidal anti-inflammatory drug.

5. The pharmaceutical composition defined by claim 4, comprising from 25 mg to 600 mg of said non-steroidal anti-inflammatory drug.

6. The pharmaceutical composition defined by claim 2, comprising from 50 mg to 60 mg of ibuprofen or pharmaceutically acceptable salt thereof.

7. The pharmaceutical composition defined by claim 6, comprising at least 100 mg of ibuprofen or pharmaceutically acceptable salt thereof.

8. The pharmaceutical composition defined by claim 3, comprising from 125 mg to 500 mg of naproxen or pharmaceutically acceptable salt thereof.

9. The pharmaceutical composition as defined by claim 1, comprising from 1 mg to 1000 mg of said non-sedating antihistamine.

10. The pharmaceutical composition as defined by claim 1, further comprising (iii) a pharmaceutically acceptable non-toxic carrier.

11. The pharmaceutical composition as defined by claim 1, in oral dosage form.

12. The pharmaceutical composition as defined by claim 11, in oral dosage tablet form.

13. The pharmaceutical composition as defined by claim 11, in oral dosage capsule form.

14. The pharmaceutical composition as defined by claim 11, in oral dosage suspension form.

15. The pharmaceutical composition as defined by claim 1, wherein said non-sedating antihistamine is AHR-11325.

16. The pharmaceutical compositon as defined by claim 1, wherein said non-sedating antihistamine is azelastine.

17. The pharmaceutical composition as defined by claim 1, wherein said non-sedating antihistamine is ebastine.

18. The pharmaceutical composition as defined by claim 1, wherein said non-sedating antihistamine is lodoxamide.

19. The pharmaceutical composition as defined by claim 1, wherein said non-sedating antihistamine is levocabastine.

20. The pharmaceutical composition as defined by claim 1, wherein said non-sedating antihistamine is mequitazine.

21. The pharmaceutical composition as defined by claim 1, wherein said non-sedating antihistamine is oxatomide.

22. The pharmaceutical composition as defined by claim 1, wherein said non-sedating antihistamine is setastine.

23. The pharmaceutical composition is defined by claim 1, wherein said non-sedating antihistamine is tazifylline.

24. A method for the treatment of cough, cold, cold-like and/or flu symptoms and the discomfort, pain, fever and general malaise associated therewith, in a mammalian organism in need of such treatment comprising administering to such organism a symptom relieving antihistaminically, analgesically and anti-inflammatory effective amount of a composition comprising (i) at least one of the propionic acid NSAIDs, ibuprofen, naproxen, benoxaprofen, flurbiprofen, fenoprofen, fenbufen, ketoprofen, indoprofen, pirprofen, carprofen, oxaprozin, pranoprofen, miroprofen, tioxaprofen, alminoprofen, tiaprofenic acid, fluprofen and bucloxic acid or pharmaceutically acceptable salt thereof, in combinatory immixture with (ii) at least one non-sedating antihistamine AHR-11325, azelastine, ebastine, lodoxamide, levocabastine, mequitazine, oxatomide, setastine, tazifylline, or pharmaceutically acceptable salt thereof.

25. A method for the treatment of cough, cold, cold-like and/or flu symptoms and the discomfort, pain, fever and general malaise associated therewith, in a mammalian organism in need of such treatment comprising administering to such organism the pharmaceutical composition as defined by claim 1.

26. A method for the treatment of cough, cold, cold-like and/or flu symptoms and the discomfort, pain, fever and general malaise associated therewith, in a mammalian organism in need of such treatment comprising administering to such organism the pharmaceutical composition as defined by claim 2.

27. A method for the treatment of an allergic reaction in a mammalian organism in need of such treatment, comprising administering to such organism an allergic symptom relieving effective amount of a composition comprising (i) at least one of the propionic acid NSAIDs, ibuprofen, naproxen, benoxaprofen, flurbiprofen, fenoprofen, fenbufen, ketoprofen, indoprofen, pirprofen, carprofen, oxaprozin, pranoprofen, microprofen, tioxaprofen, alminoprofen, tiaprofenic acid, fluprofen and bucloxic acid or pharmaceutically acceptable salt thereof, in combinatory immixture with (ii) at least one of the non-sedating antihistamines, AHR-11325, azelastine, ebastine, lodoxamide, levocabastine, mequitazine, oxatomide, setastine, tazifylline, or pharmaceutically acceptable salt thereof.

28. The method as defined by claim 27, said allergic reaction comprising coryza or rhinitis.

29. The method as defined by claim 27, wherein said propionic acid NSAID is ibuprofen.

* * * * *